United States Patent [19]

Bessin

[11] 4,246,277
[45] Jan. 20, 1981

[54] LOWERING THE CONCENTRATION OF PLASMA TRIGLYCERIDES

[75] Inventor: Pierre Bessin, Chilly Mazarin, France

[73] Assignee: Albert Rolland S.A., Paris, France

[21] Appl. No.: 51,241

[22] Filed: Jun. 22, 1979

[51] Int. Cl.³ .............................................. A61K 31/34
[52] U.S. Cl. ................................................. 424/285
[58] Field of Search .............................. 424/275, 285

[56] References Cited

U.S. PATENT DOCUMENTS

| | | | |
|---|---|---|---|
| 4,029,808 | 6/1977 | Thuillier et al. | 424/275 |
| 4,148,911 | 4/1979 | Bessin | 424/275 |

OTHER PUBLICATIONS

Bessin et al., CR Acad. Sci. Paris, vol. 281, Ser. D, 1975, pp. 463–466.

Primary Examiner—Anna P. Fagelson

[57] ABSTRACT

The present invention relates to a method of lowering the concentration of plasma triglycerides of a subject in need thereof, which comprises administering an effective but non toxic amount of each isomer or a mixture thereof of compound

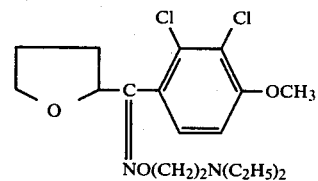

or pharmaceutically acceptable addition salt of said amine formed with an acid.

2 Claims, No Drawings

LOWERING THE CONCENTRATION OF PLASMA TRIGLYCERIDES

This invention relates to a method of lowering the concentration of plasma triglycerides in a hyperlipidemic subject by administering pharmaceutical compositions containing as active ingredient non toxic but effective quantities of each stereoisomer, or mixtures of the two of (2,3-dichloro-4-methoxy) phenyl 2-furyl ketone O-(diethylaminoethyl)oxime of formula I or their salts with pharmaceutically acceptable acids, for example hydrochloric, methane sulfonic acids.

This oximino compound

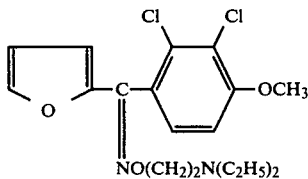

and its preparation is described in U.S. Pat. No. 4,029,808. This compound is known as a peripheral and coronary vasodilatator and so useful to treat coronary heart disease; in such a disease high plasma lipid concentrations is very frequent and therefore it is useful, and unexpected, to treat these 2 disorders with the same compound. The hypolipidemic activity of (2,3-dichloro-4-methoxy)phenyl 2-furyl ketone O-(diethylaminoethyl)oxime or its salt is demonstrated in obese rats, fatty breed, by oral administration of the methane sulfonate of the compound at a dose of 100 mg/kg/day for 7 days. The eighth day, animals are killed and the blood taken. Plasma triglycerides, cholesterol and lipids are determined by standard methods. The results are summarized in Table I.

TABLE I

| | (Isomer Z) Effect of compound I on plasma liquid concentrations of Fatty rat | |
|---|---|---|
| | Control | Treated |
| Plasma lipids (mg/100 ml) | 1012 ± 201 | 626 ± 180 |
| Plasma triglycerides (mg/100 ml) | 506 ± 98 | 174 ± 35.2 |

The isomer E gives equivalent results.

Compared to controls, the treated animals showed a significant reduction in plasma lipids and triglycerides but plasma cholesterol concentrations were not significantly affected.

The hypolipidemic compositions of this invention are prepared in conventional dosage unit forms by incorporating the compound of formula I, as a liquid, or as one of its solid pharmaceutically acceptable salt thereof with a pharmaceutical carrier according to accepted procedures, to obtain oral or injectable form.

The method of treatment according with this invention comprises administering to a patient in need thereof each stereoisomer or a mixture thereof of (2,3-dichloro-4-methoxy)phenyl 2-furyl ketone O-(diethylaminoethyl)oxime in an active but non toxic amount selected from 25 mg to 200 mg per dosage unit.

What is claimed is:

1. A method of lowering the concentration of plasma triglycerides of a subject in need thereof, which comprises administering a therapeutically effective but non toxic amount of at least one of the two stereoisomers or a mixture thereof of a compound having the formula

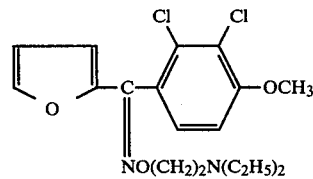

or pharmaceutically acceptable addition salt of said amine formed with an acid.

2. The method of claim 1 in which a daily dosage from 50 mg to 600 mg of active ingredient is administered.

* * * * *